United States Patent [19]

Ginsburg et al.

[11] Patent Number: 5,225,330
[45] Date of Patent: Jul. 6, 1993

[54] DIAGNOSTIC KIT AND DIAGNOSTIC METHOD UTILIZING CARBOHYDRATE RECEPTORS

[75] Inventors: Victor Ginsburg, Bethesda; Howard C. Krivan; David D. Roberts, both of Rockville, all of Md.

[73] Assignee: The United States of America as represented by the Department of Health and Human Services, Washington, D.C.

[21] Appl. No.: 417,691

[22] Filed: Oct. 5, 1989

Related U.S. Application Data

[63] Continuation-in-part of Ser. No. 277,634, Nov. 28, 1988, Pat. No. 5,089,479, and a continuation-in-part of Ser. No. 226,445, Aug. 1, 1988.

[51] Int. Cl.$^5$ .................... G01N 33/569; G01N 33/53
[52] U.S. Cl. .................... 435/7.32; 435/7.34; 435/7.31; 435/7.8; 435/7.92; 435/29; 436/534; 436/519
[58] Field of Search .................... 435/7.32–7.37, 435/7.8, 7.92, 29, 34, 261, 810, 975, 7.31; 436/519, 520, 531, 533, 534

[56] References Cited

U.S. PATENT DOCUMENTS

| | | | |
|---|---|---|---|
| 4,280,816 | 7/1981 | Elahi | 422/57 |
| 4,374,925 | 2/1983 | Litman et al. | 435/5 |
| 4,391,904 | 7/1983 | Litman et al. | 435/188 |
| 4,727,019 | 2/1988 | Valkirs et al. | 435/5 |
| 4,774,174 | 9/1988 | Giegel et al. | 435/5 |
| 4,863,852 | 9/1989 | Wilkins et al. | 435/34 |
| 4,921,788 | 5/1990 | Deutsch | 435/6 |
| 4,959,303 | 9/1990 | Milburn et al. | 435/29 |
| 5,089,479 | 2/1992 | Krivan et al. | 514/25 |

FOREIGN PATENT DOCUMENTS 0323692 8/1988 European Pat. Off. .

OTHER PUBLICATIONS

Krivan et al., Proc. Natl. Acad. Sci., USA, 85, (Aug. 1988), pp. 6157–6161.
Krivan et al., Arch. Biochem. Biophys., 260(1):493–496, (Jan. 1988).
Krivan et al., Abstracts of the Annual Meeting of the American Society for Microbiology, 88, abs. no. B-163, (1988).
Krivan et al., "Cell Surface Carbohydrates as Adhesion Receptors for Many Pathogenic and Opportunistic Microorganisms", in *Microbial Adhesion and Invasion*, Hook et al., eds., 1–13, (1992).
Taki et al., J. Biochem., 91(5):1813–1816, (1982).
Nakamura et al., J. Biochem., 101(4):825–835, (1987).
Stromberg et al., Proc. Natl. Acad. Sci. USA, 85:4902–4906, (Jul. 1988).
Fukuda et al., J. Biol. Chem., 260(2):1067–1082, (Jan. 25, 1985).
Hofstetter et al., J. Immunol. Methods, 57:99–109, (1983).
Hansson et al., Anal. Biochem., 146:158–163, (1985).
Karlsson et al., Methods in Enzymology, vol. 138:220–232, (1987).
Microparticle Immunoassay Techniques, 2nd Ed., Saradyn, Inc., pp. 4–7, 41–49.
Kyogashima et al., Archives of Biochemistry and Biophysics, vol. 270, No. 1, Apr. 1989.
Product brochure, "Tandem® Icon Strep A", Hybritech, (1986).
Jimenez et al., 1989 ASM Annual Meeting, New Orleans, La., May 14–18, 1989, Abstract.
Roberts et al., Abstract Glycoconjugate Journal, vol. 5, p. 350, (1988).
De Man et al., Journal of Clinical Microbiology, vol. 25, No. 2, pp. 401–406, Feb. 1987.
Oellerich, J. Clin. Chem. Clin. Biochem., vol. 22, pp. 895–904, (1984).
Kyogashima et al., Biol. Abstr., vol. 87, No. 11, Abstract No. 116420, (1989).
Magnani et al., Biol. Abstr., vol. 71, No. 11, Abstract No. 74443, (1980).
Roberts et al., Biol. Abstr., vol. 88, No. 4, Abstract No. 38337, (1990).
Deal et al., Biological Abstracts, vol. 90, Abstract No. 100406, (1990).
Krivan et al., Abstr. Ann. Meet. Am. Soc. Microbiol., 88(0), 1988, 56.
Roberts et al., *J. Biol. Chem.*, 264(16):9289, 1989.

*Primary Examiner*—Esther L. Kepplinger
*Assistant Examiner*—Carol E. Bidwell
*Attorney, Agent, or Firm*—Birch, Stewart, Kolasch & Birch

[57] ABSTRACT

A diagnostic kit for detecting the presence of microorganisms, comprising an insoluble substrate; and a carbohydrate receptor immobilized on the insoluble substrate, the carbohydrate receptor being capable of adsorbing microorganisms; and a labelled reagent useful for detecting the presence of microorganisms bound to the carbohydrate receptors and a method for detecting the presence of specified microorganisms in a sample, which comprises contacting a sample to be tested with carbohydrate receptors immobilized on an insoluble substrate; and determining the extent of binding of microorganisms in the sample to the carbohydrate receptors by use of a labelled reagent.

16 Claims, 8 Drawing Sheets

FIG. 2
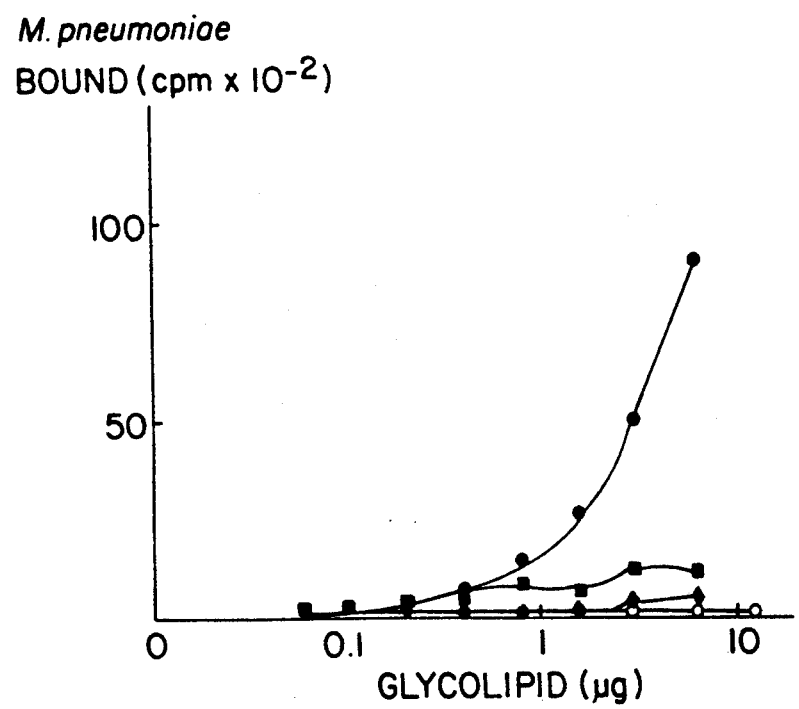
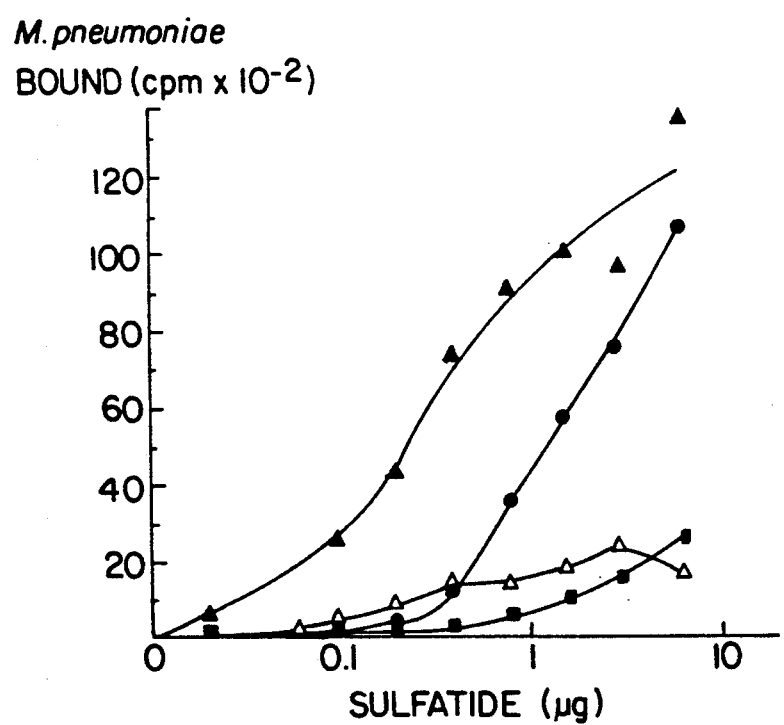
FIG. 3

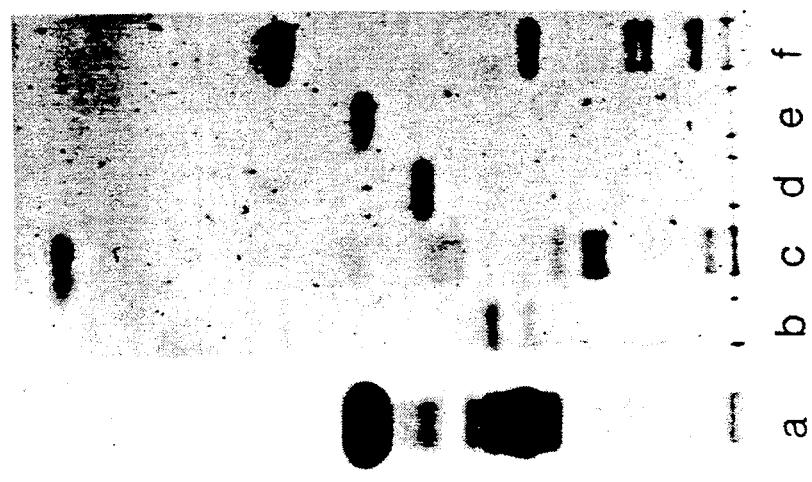
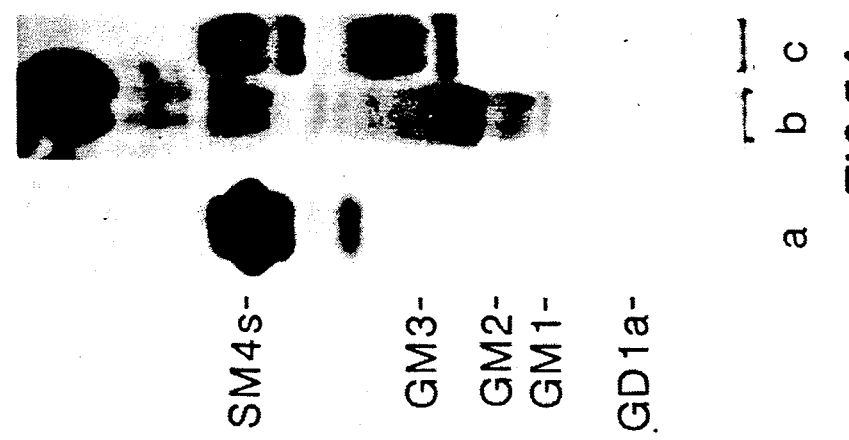

DIAGNOSTIC KIT AND DIAGNOSTIC METHOD UTILIZING CARBOHYDRATE RECEPTORS

CROSS-REFERENCE TO RELATED APPLICATIONS

This application is a continuation-in-part of copending application Ser. Nos. 07/277,634 filed Nov. 28, 1988 now U.S. Pat. No. 5,089,479 issued Feb. 18, 1992 and 07/226/445 filed Aug. 1, 1988. These applications are hereby incorporated by reference.

BACKGROUND OF THE INVENTION

Devices and techniques for the rapid detection of certain bacteria are known in the art. For example, the Tandem Icon Strep A test kit utilizes a procedure wherein Streptococcus antigens are extracted from a sample and are bound to a membrane. A colorometric test is then conducted whereby an enzyme conjugated to an antibody is bound to the antigen and thereafter a substrate for the enzyme is contacted with the enzyme. If the enzyme is present, the substrate turns color thereby indicating a positive test. Although this is a useful technique, a need exists for a test having a longer shelf life, which is cheaper and which may be more versatile.

SUMMARY OF THE INVENTION

The present invention is directed to a diagnostic device for adsorbing microorganisms which comprises an insoluble substrate and a carbohydrate receptor capable of adsorbing bacteria bound to the insoluble substrate. The invention also relates to a method for detecting the presence of specified microorganisms in a sample which comprises contacting a sample to be tested with carbohydrate receptors bound to an insoluble substrate and determining the extent of binding of the microorganism in the sample to the carbohydrate receptors bound to the substrate.

Various insoluble substrates to which the carbohydrate receptors can be bound may be used. The substrate should be capable of easily binding the carbohydrate receptors without interfering with the diagnostic test to be conducted. Possible substrates include glass; thin layer chromatographic materials such as silica gel; synthetic plastic materials such as polyvinyl chloride, polystyrene, polypropylene and polyethylene. The substrates may be in the form of flat plates, glass beads, latex beads, thin layers on another substrate, microtiter plates, Petri dishes, etc. The substrate may also be in the form of a membrane or film of either a porous or nonporous nature.

The carbohydrate receptor which is bound to the substrate must bind to the microorganism to be tested. Carbohydrate receptors which selectively bind to various pathogenic gram positive and gram negative bacteria and pathogenic yeast or fungi may be utilized in connection with the present invention. Specifically, it is contemplated that carbohydrate receptors which bind to pathogenic gram positive bacteria such as Streptococcus and Staphylococcus, pathogenic gram negative bacteria such as Mycoplasma, Pseudomonas and Escherichia and pathogenic yeast such as Cryptococcus may be utilized in accordance with the present invention.

The term "carbohydrate receptor" means a carbohydrate compound or carbohydrate moiety of a compound which selectively binds to microorganisms. The carbohydrate receptor may have as few as one sugar unit or may have several sugar units.

The monosaccharide unit galactose 3-sulfate contained in sulfatide is an example of a single sugar unit which may function as a carbohydrate receptor. The disaccharide sequence GalNAc$\beta$1-4Gal may also function as a carbohydrate receptor. The trisaccharide sequence Gal$\beta$1-4Glc$\beta$1-1Cer may act as a carbohydrate receptor for Cryptococcus. Other structures which may function as carbohydrate receptors include sialyl $\alpha$(2-3) galactose $\beta$(1-4) N-acetylglucosamine for *Mycoplasma pneumoniae*.

The carbohydrate receptor may be part of a glycolipids including sulfated glycolipids such as sulfatide, asialo GM1 and asialo GM2.

Particularly preferred glycolipids are those which contain a terminal Gal(3SO$_4$) $\beta$1-residue.

Glycolipids tested for ability to bind various bacteria include the following:

| Name | Structure |
|---|---|
| Sulfatide (SO$_4$) | Gal(SO$_4$)$\beta$1-1Cer |
| Sulfatide (3SO$_4$) | Gal(3SO$_4$)$\beta$1-1Cer |
| Sulfatide (6SO$_4$) | Gal(6SO$_4$)$\beta$1-1Cer |
| Lactosylsulfatide | Gal(3SO$_4$)$\beta$1-4Glc$\beta$1-1Cer |
| Seminolipid | Gal(3SO$_4$)$\beta$1-3alkylacrylglycerol |
| Glucosylceramide (CMH) | Glc$\beta$1-1Cer |
| Lactosylceramide (CDH) | Gal$\beta$1-4Glc$\beta$1-1Cer |
| Lacto-N-triaosylcer | GlcNAc$\beta$1-3Gal$\beta$1-4Glc$\beta$1-1Cer |
| Paragloboside | Gal$\beta$1-4GlcNAc$\beta$1-3Gal$\beta$1-4Glc$\beta$1-1Cer |
| $\alpha$-Galactosylparagloboside | Gal$\alpha$1-3Gal$\beta$1-4GlcNAc$\beta$1-3Gal$\beta$1-4Glc$\beta$1-1Cer |
| Galactosylceramide (CMH) | Gal$\beta$1-1Cer |
| SO$_4$-Glucuronosylparagloboside | GlcA(3SO$_4$)$\beta$1-3Gal$\beta$1-4GlcNAc$\beta$1-3Gal$\beta$1-4Glc$\beta$1-1Cer |
| Trihexosylceramide (CTH) | Gal$\alpha$1-4Gal$\beta$1-4Glc$\beta$1-1Cer |
| Asialo GM2 | GalNAc$\beta$1-4Gal$\beta$1-4Glc$\beta$1-1Cer |
| Globoside (GL4) | GalNAc$\beta$1-3Gal$\alpha$1-4Gal$\beta$1-4Glc$\beta$1-1Cer |
| Asialo GM1 | Gal$\beta$1-3GalNac$\beta$1-4Gal$\beta$1-4Glc$\beta$1-1Cer |
| GM3 | NeuAc$\alpha$2-3Gal$\beta$1-4Glc$\beta$1-1Cer |
| GM3 (NeuGc) | NeuGc$\alpha$2-3Gal$\beta$1-4Glc$\beta$1-1Cer |
| GM2 | GalNAc$\beta$1-4[NeuAc$\alpha$2-3]Gal$\beta$1-4Glc$\beta$1-1Cer |
| GM1 | Gal$\beta$1-3GalNAc$\beta$1-4[NeuAc$\alpha$2-3]Gal$\beta$1-4Glc$\beta$1-1Cer |
| Sialylparagloboside | NeuAc$\alpha$2-3Gal$\beta$1-4GlcNAc$\beta$1-3Gal$\beta$1-4Glc$\beta$1-1Cer |
| Sialylparagloboside (NeuGc) | NeuGc$\alpha$2-3Gal$\beta$1-4GlcNAc$\beta$1-3Gal$\beta$1-4Glc$\beta$1-1Cer |
| Sialylneolactofucopentaosylcer | NeuAc$\alpha$$\alpha$2-3Gal$\beta$1-4[Fuc$\alpha$1-3]GlcNAc$\beta$1-3Gal$\beta$1-4Glc$\beta$1-1Cer |

-continued

| Name | Structure |
| --- | --- |
| GD1a | NeuAcα2-3Galβ1-3GalNAcβ1-4[NeuAcα2-3]-Galβ1-4Glcβ1-1Cer |
| GD1b | Galβ1-3GalNAcβ1-4[NeuAcα2-8Neuα2-3]Galβ1-4Glcβ1-1Cer |
| GT1b | NeuAcα2-3Galβ1-3GalNacβ1-4[NeuAcα2-8NeuAcα2-3]Galβ1-4Glcβ1-1Cer |
| Sialylneolacto-hexasolycer | NeuGcα2-3Galβ1-4GlcNAcβ1-3Galβ1-4GlcNAcβ1-3Galβ1-4Glcβ1-1Cer |
| Fucosylasialo-GM1 | Fucα1-2Galβ1-3GalNAcβ1-4Galβ1-4Glcβ1-1Cer |
| Asialo-Cad | GalNAcβ1-4Galβ1-4GlcNAcβ1-3Galβ1-4Glcβ1-1Cer |
| Forssman | GalNAcα1-3GalNAcβ1-3Galα1-4Galβ1-4Glcβ1-1Cer |
| Cad | GalNAcβ1-4(NeuAcα2-3)Galβ1-4GlcNAcβ1-3Galβ1-4Glcβ1-1Cer |
| I-Active Sialyl-lactoisooctaosylcer | Galα1-3Galβ1-4GlcNAcβ1<br>⁶Galβ1-4GlcNAcβ1-3Galβ1-4Glcβ1-1Cer<br>NeuAcα2-3Galβ1-4GlcNAcβ1 3 |
| I-active Lacto-isooctaosylcer | Galβ1-4GlcNAcβ1  6<br>  Galβ1-4GlcNAcβ1-3Galβ1-4Glcβ1-1Cer<br>Galβ1-4GlcNAcβ1   3 |
| I-active Gal₂-lactoisooctaosylcer | Galα1-3Galβ1-4GlcNAcβ1<br>⁶Galβ1-4GlcNAcβ1-3Galβ1-4Glcβ1-1Cer<br>Galα1-3Galβ1-4GlcNAcβ1   3 |

Trivial names and structures are represented according to recommendations in IUPAC-IUB Joint Commission on Biochemical Nomenclature, Eur. J. Biochem., 159, 1-6 (1986) and references cited therein; cer, ceramide.

Glycolipids which binds to *Escherichia coli* include:

| Name | Structure |
| --- | --- |
| N-glycolyl-GM3 | NeuGcα2-3Galβ1-4Glcβ1-1Cer |
| N-glycolylsialoparaglobosirde | NeuGcα2-3Galβ1-4GlcNAcβ1-3Galβ1-4Glcβ1-1Cer |

The binding of these two glycolipids to *Escherichia coli* is described by Kyogashima et al, Archives of Biochemistry and Biophysics, 270, No. 1, 391-397 (April 1989) which is hereby incorporated by reference.

The carbohydrate receptor may be part of a glycoprotein such as laminin, fetuin, human chorionic gonadotropin, human platelet thrombospondin and derivatives of these glycoproteins. Particularly preferred glycoproteins are those with α2-3-linked sialic acid.

The glycolipid lactosylceramide which has the structure Galβ1-4Glcβ1-1Cer binds to the yeastlike fungus *Cryptococcus neoformans*.

The carbohydrate receptor should be bound to the substrate in an amount sufficient to and in a manner which allows binding of the bacteria to be diagnosed to the carbohydrate receptor. From a practical point of view, the carbohydrate receptor will usually be present in an amount of at least 0.1 pmol/mm², more preferably at least 1 pmol/mm² of surface area of the substrate. As far as the upper limit of the concentration of the carbohydrate receptor on the substrate, the carbohydrate receptor can be bound up to the saturation density of the substrate. The saturation density of sulfatide on polystyrene is about 3 pmol/mm². The carbohydrate receptor can be bound as a molecular monolayer which substantially completely covers the surface area of the substrate. Use of more than a molecular monolayer of carbohydrate receptors bound to the substrate may result in a waste of materials and may result in inefficient binding of the carbohydrate receptor to the substrate. A preferred range for the density of the carbohydrate receptor bound to the substrate is 0.1 pmol/mm² to the saturation density of the carbohydrate receptor, more preferably 0.1 to 3 pmol/mm². The actual concentration of carbohydrate receptor bound to a given substrate will depend upon the particular bacteria to be diagnosed and the binding efficiency of the carbohydrate receptor to the particular bacteria.

The carbohydrate receptor may be bound to the substrate in any suitable manner. Covalent or non-covalent (e.g., hydrophobic) bonding may be used to bind the carbohydrate receptor to a substrate. For example, the lipid portion of glycolipids will hydrophobically bond to certain plastic substrates leaving the carbohydrate receptor, i.e., the sugar or glyco group, the available to bind to microorganisms. Alternatively, a carbohydrate receptor may be covalently bonded to a substrate. Other forms of bonding such as ionic bonding may be used.

The carbohydrate receptor may also be bound to particles, such as latex particles, which are thereafter immobilized on by imbedding in or binding to a porous membrane. The latex particles may be of a size which can be embedded by pressure into the pores of the porous membrane. Thus, for example, the average particle size of the latex particles may be about the same as, or slightly smaller than, the average surface pore size of said porous membrane. Alternatively, the particles may be bound to any porous or liquid permeable material such as a screen, net, etc. A material such as a binder may be used to bind the particles to the support as long as the binder does not interfere with the ability of the carbohydrate receptors to bind microorganisms. In another embodiment, the particles may be packed in a container such as a column having an inlet and an outlet, whereby the sample to be tested and the necessary diagnostic reagents may be contacted with the particles when passing through the container.

Various samples can be tested for the presence of bacteria by the method of the present invention. For diagnosis of disease and/or infections a body sample from a patient suspected of being infected will normally be diluted in an appropriate solution such as physiological saline and this solution will then be contacted with the diagnostic device containing the substrate and the carbohydrate receptors. When testing for the presence of pathogens in the oral cavity of a patient to be tested, a cotton swab or other material will be swabbed in the inside of the patient's mouth and this swab will be placed in a sterile solution whereby bacteria in the cotton swab will be released from the swab into the solution. This solution will then be tested for the presence of bacteria. It is also possible to test for bacteria in body fluids such as sputum, urine, saliva and blood.

The present invention may also be utilized to test for other types of bacteria such as bacteria which may contaminate environments which should be kept sterile such as hospital operating rooms, drug and medical device manufacturing facilities, food manufacturing facilities, etc. In such situations, the area to be tested will usually be swabbed and the swab will be placed into a sterile solution to release the bacteria in much the same manner as when a swab sample is taken from a patient's mouth. This solution can then be contacted with the device of the present invention.

The solution suspected of containing bacteria is contacted with the substrate containing the carbohydrate receptors described hereinabove. Preferably, the solution is contacted with the substrate until or before equilibrium is reached, e.g., 1 to 90 minutes, more preferably 5 to 60 minutes at a temperature of 0° to 40° C., preferably 4° to 37° C., depending on the microorganism to be tested. For example, the preferred temperature for Mycoplasma appears to be about 37° C. whereas the preferred temperature for Clostridium appears to be about 4° C. The precise time and temperature conditions are selected to provide sufficient time for the bacteria to adsorb to the carbohydrate receptors to a degree sufficient to allow for accurate testing. The sample to be tested may be dissolved and/or diluted with various liquids such as physiological saline, etc.

After the solution has been contacted with the substrate containing the carbohydrate receptors for a time sufficient to allow the bacteria to bind to the carbohydrate receptors, the substrate is washed to remove all unbound materials.

A test is then conducted to determine the presence of the bacteria bound to the carbohydrate receptors on the substrate. Various tests to accomplish this purpose are known in the art such as the enzyme linked immunosorbent assay (ELISA), a radioimmune assay test, direct or indirect fluorescent antibody test, etc. Basically, the substrate containing the carbohydrate receptors and suspected of containing bacteria bound thereto is contacted with a material which binds to the bacteria to be tested. Such materials include, for example, antibodies against the bacteria or a carbohydrate receptor which binds to the bacteria.

The antibody or carbohydrate receptor may be "labelled" with a substance which may be easily detected. For example, the antibody or carbohydrate receptor may be conjugated with an enzyme, radioactive material or element or fluorescent material. If the antibody or carbohydrate receptor is conjugated with an enzyme, the substrate is thereafter contacted with a substrate for the enzyme which preferably turns color upon contact with the enzyme thereby indicating a positive reaction. The antibody or carbohydrate receptor to be used should be one which reacts with the bacteria but which does not react with the coated substrate or with the carbohydrate receptors bound to the substrate thereby preventing a false positive reading. If the enzyme or carbohydrate receptor is radioactively labelled, then the presence of radioactivity on the substrate should be measured. It is also possible that the enzyme or carbohydrate receptor may be fluorescently labelled. In this situation the treated substrate should be exposed to ultraviolet light to determine the presence of the fluorescent labelled material bound to the substrate.

Alternatively, the test may include the following steps:

(I) providing a carbohydrate receptor on a substrate to provide a coated surface on said substrate;

(II) contacting a patient's bodily fluids or tissue extracts with said coated substrate surface to selectively bind microorganisms in said patient's bodily fluids or tissue extracts to said coated surface;

(III) contacting, after step (II), a first antibody against said microorganism with said coated surface, to bind said second antibody to said coated surface when said microorganism has previously bound to said coated surface in step II;

(IV) contacting, after step III, an enzyme labeled antibody which is reacted with said first antibody with said coated surface, to bind said enzyme labeled antibody to said coated surface when said first antibody has previously bound to said coated surface in step III; and (V) contacting, after step IV, said coated substrate with a chemical (enzyme label indicator) which indicates the presence of said enzyme labeled antibody bound to said coated surface.

BRIEF DESCRIPTION OF THE DRAWINGS

FIG. 2. Binding of $M.$ $pneumoniae$ to purified glycolipids. Lipids in 25 μl of methanol containing 0.1 μg each of the auxiliary lipids cholesterol and phosphatidylcholine were evaporated in flat bottom wells of polyvinylchloride microtiter plates. The wells were blocked with 1% albumin for 1 h, washed twice with RPMI-BSA, and incubated at 25° C. with 25 μl of [$^3$H]-$M.$ $pneumoniae$ (approximately $10^5$ cpm). After 2 h, the wells were washed five times with saline, cut from the plate, and bound radioactivity quantified in a scintillation counter. In control experiments organisms were incubated with auxiliary lipids only to correct for nonspecific binding (typically <1% of the total radioactivity added). $M.$ $pneumoniae$ binding was determined in RPMI-BSA for sulfatide (solid circles), lactosylceramide (solid squares), paragloboside (solid diamonds), and cholesterol sulfate, ceramide trihexoside, globoside, GM1, GM2, or GM3 (open circles).

FIG. 3. Energy and temperature dependent binding of $M.$ $pneumoniae$ to sulfatide. Microtiter wells were coated with sulfatide and blocked with albumin as described in the legend of FIG. 2. Binding of [$^3$H]-$M.$ pneumoniae was determined in RPMI-BSA for 2 h at 4° C. (solid square), 25° C. (solid circle), 37° C. (solid triangle), and at 37° C. in BSA without RPMI (open triangle).

FIG. 5. Identification of sulfatide synthesized by WiDr adenocarcinoma cells. WiDr cells were metabolically labeled with [$^{35}$S]-sulfate as described in Materials and Methods. Neutral acidic lipids were chromatographed on silica gel high performance thin layer plates developed in chloroform/methanol/0.25% KCl in water, 5:4:1 (Panel A) or chloroform/methanol/acetone/acetic acid/water, 8:2:4:2:1 (Panel B). The lipids were detected by autoradiography (lane a) or orcinol reagent (lanes b-f). Panel A, [$^{35}$S]-labeled acidic lipids from $10^6$ WiDr cells (lane a), neutral (lane b) and acidic (lane c) lipids from 30 mg wet weight of WiDr cells. The orcinol positive sulfatide band is indicated by the arrow (←). Migration of reference glycolipids is indicated in the left margin: sulfatide, GM3, GM2, GM1, GD1a, GD1b, and GT1b. Panel B, [$^{35}$S]-labeled acidic lipids from $10^6$ WiDr cells (lanes a & c), bovine brain sulfatide (land b), seminolipid (lane d), cholesterol 3-sulfatide (lane e), and neutral glycolipid standards from top to bottom CMH, CDH, CTH, and GL4 (lane f). For abbreviations, see footnote 1 and Table I.

DETAILED DESCRIPTION OF THE INVENTION

Figure 1:
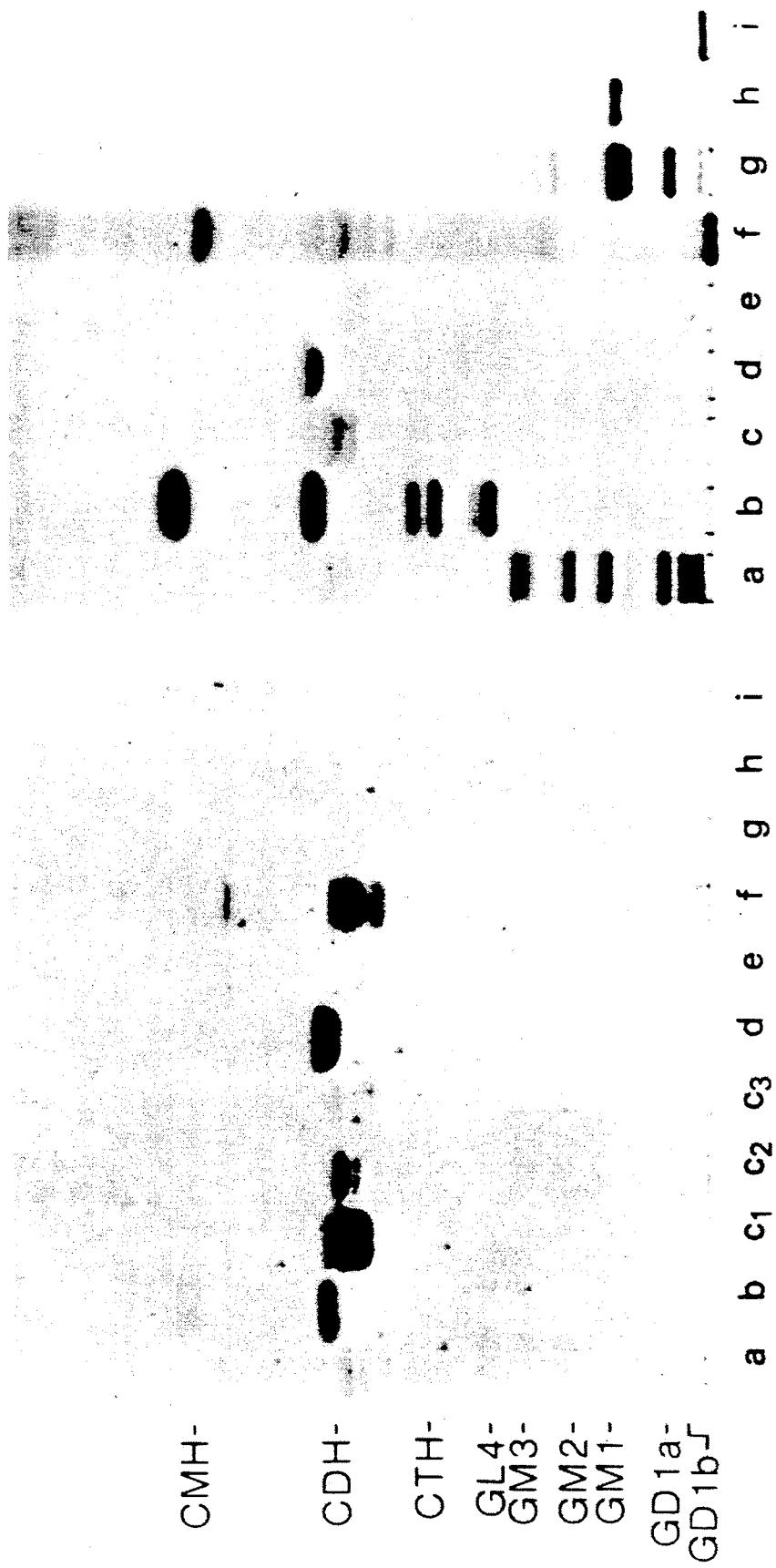
FIG. 1. Binding of $M.$ $pneumoniae$ to glycolipids separated by thin layer chromatography. Glycolipids were chromatographed on aluminum-backed silica gel HPTLC plates developed in chloroform/methanol/0.25% $CaCl_2$ in water, 60:35:8. The plates were coated with plastic, soaked in Tris-BSA, and incubated for 3 h at 25° C. with [$^3$H]-palmitate-labeled $M.$ $pneumoniae$ suspended in RPMI 1640 containing 1% BSA and 25 mM HEPES, pH 7.3, as described in Materials and Methods (Panel A), or sprayed with orcinol reagent to identify glycolipids (Panel B). Lane a, acidic glycolipid standards sulfatide (0.5 μg), GM3 (2 μg), GM2 (2 μg), GD1a (2 μg), GD1b (2 μg), GT1b (2 μg); lane b, neutral standards galactosyl ceramide (4 μg), lactosylceramide (4 μg), globotriaosylceramide (2 μg), and globotetraosylceramide (2 μg); lanes c and c:, sulfatide (2 μg), $c_2$ (0.5 μg), and $c_3$ (0.1 μg); lane d, seminolipid (2 μg); lane e, cholesterol 3-sulfate (2 μg); lane f, human trachea acidic glycolipids from 100 mg wet weight of tissue; lane g, monosialoganglioside from 100 mg wet weight of bovine erythrocytes; lane h, α2-3sialylparagloboside (2 μg); lane i, I-active monosialylganglioside from bovine erythrocytes (2 μg). For abbreviations, see footnote 1 and Table I.
Figure 4:
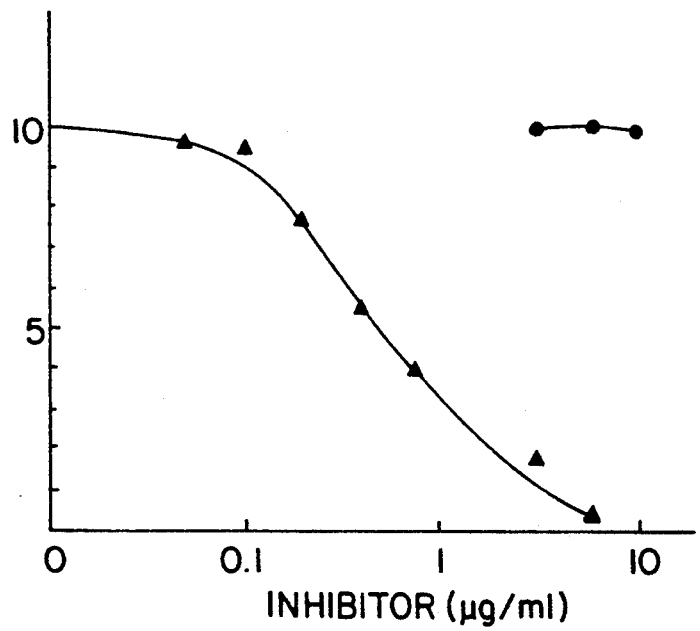
FIG. 4. Inhibition of M. pneumoniae binding to sulfatide by dextran sulfate. Polysaccharides were serially diluted with 25 μl of RPMI-BSA in microtiter wells previously coated with 1 μg of purified sulfatide. Binding was determined after incubation for 2 h at 37° C. with 25 μl of [$^3$H]-M. pneumoniae with the indicated concentration of dextran (solid circle) or dextran sulfate (solid triangle).

The term "antibody" as used herein refers to polyclonal antibodies or monoclonal antibodies. Although polyclonal antibodies are preferred, monoclonal antibodies having appropriate binding ability to the desired "antigens" may be substituted therefor.

The term "bodily fluid" refers to any human liquid product as for example sputum, saliva, plasma, peritoneal fluid, cerebrospinal fluid and so forth.

The term "enzyme labelled antibody" as used herein refers to an antibody labelled with an enzyme such as alkaline phosphatase, peroxidase, or the like, which is capable of reaction with a chemical indicator as defined below.

The term "enzyme label indicator" as used herein refers to chemical indicators for indicating, preferably by color change, the presence of enzyme labelled antibody bound to the substrate's coated surface. For example, p-nitrophenol phosphate is one such enzyme label indicator for the enzyme alkaline phosphatase.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

EXAMPLE 1

Materials

Dextran sulfate (M, 500,000, lot 44F-0408 and M, 5,000, lot 77F-0634), fucoidin, colominic acid (E. coli), hyaluronate, dipalmitoylphosphatidylcholine (synthetic), cholesterol (Grade I, 99%), cholesterol 3-sulfate, and bovine serum albumin (A7030 fatty acid and globulin free), were from Sigma. Bovine lung heparin (160 units/mg) was from the UpJohn Co. RPMI 1640 medium was purchased from Biofluids.

Glycolipids

Bovine brain sulfatide (galactosyl ceramide-I$^3$-sulfate), ceramide monohexoside, ceramide trihexoside, globoside, and gangliosides GM1 and GD1a were obtained from Supelco. Lactosylceramide and glucosylceramide were from Calbiochem. Other reference gangliosides were from Bachem, Inc. Seminolipid (β-galactosylalkylacylglycerol-I$^3$-sulfate) was isolated from bovine testes (Pel-Freez Biologicals) as previously described (Roberts, D. D., Wewer, U. M., Liotta, L. A., and Ginsburg, V., Cancer Res., 48, 3367-3373 (1988)). Galactosyl ceramide-I$^6$-sulfate was prepared as previously described by sulfation of galactosyl ceramide (Roberts, D. D., Rao, C. N., Liotta, L. A., Gralnick, H. R., and Ginsburg, V., J. Biol. Chem., 261, 6872-6877 (1986)). Sulfated glucuronosylparagloboside (IV$^3$-[3'SO$_3$GlcA]- nLcOse$_4$Cer) was purified from human peripheral nerve (Chou, D. K. H., Ilyas, A. A., Evans, J. E., Costello, C., Quarles, R. H., and Jungalwala, F. B., J. Biol. Chem., 261, 11717-11725 (1986)). Lactosylceramide-II$^3$-sulfate, GM3, and sialyllactofucopentaosyl-(III)-ceramide were purified from human kidney (Martensson, E., *Biochim. Biophys. Acta*, 116, 521–531 (1966); Rauvala, H., *J. Biol. Chem.*, 251, 7517–7520 (1976); Hanfland, P., Egge, H., Dabrowski, U., Kuhn, S., Roelche, D. and Dabrowski, J., *Biochemistry*, 20, 5310–5319 (1981)). α-Galactosylparagloboside (IV$^3$Galn-LcOse$_4$Cer) and the I-active α-Gal$_2$lactoisooctaosylceramide were purified from rabbit erythrocytes (Pel-Freez) (Watanabe, K., Hakomori, S., Childs, R. A., and Feizi, T., *J. Biol. Chem.*, 254, 3221–3228 (1979)). Lactoisooctaosylceramide was prepared from the latter lipid by treatment with coffee bean α-galactosidase. α2-3-Sialylparagloboside (NeuGc), α2-3-sialyllactoneohexaosylceramide, GM3 (NeuGc), and an I-active ganglioside were prepared from bovine erythrocytes (Watanabe, K., Powell, M. E., and Hakomori, S., *J. Biol. Chem.*, 254, 8223–8228 (1979)). α2-3-Sialylparagloboside (NeuAc) was isolated from type O human erythrocytes (Ando, S., Kon, K., Isobe, M., Nagai, Y., and Yamakawa, T., *J. Biochem.*, 79, 625–632 (1976)). Paragloboside and lactoneohexaosylceramide were prepared by desialylation of the respective gangliosides with 1M formic acid for 60 min. at 100° C. Asialo-GM1 and asialo-GM2 were prepared as previously described (Krivan, H. C., Roberts, D. D., and Ginsburg, V., *Proc. Natl. Acad. Sci.*, 85, 6157–6161 (1988)). Lacto-N-triaosylceramide was prepared by digestion of paragloboside with bovine testes β-galactosidase (Boehringer Mannheim). The identities of the neolacto-series glycolipids was confirmed by immunostaining with monoclonal antibody My-28 before and after neuraminidase digestion (Spitalnik, S. L., Schwartz, J. F., Magnani, J. L., Roberts, D. D., Spitalnik, P. F., Civin, C. I., and Ginsburg, V., *Blood*, 66, 319–326 (1985)). Concentrations of galactosyl ceramide I$^6$-sulfate, galactosyl ceramide I$^3$-sulfate, cholesterol sulfate, glucosylceramide, galactosylceramide, lactosylceramide, asialo-GM1, and asialo-GM2 were determined by dry weight. Other sulfated glycolipids were determined by the dye-binding assay of Kean (Kean, E. L., *J. Lipid Res.*, 9, 319–327 (1968)) as modified by Tadano-Aritomi and Ishizuka (Tadano-Aritomi, K., and Ishizuka, I., *J. Lipid Res.*, 24, 1368–1375 (1983)). The concentrations of the other neutral and acidic glycolipids listed in Table I were determined by densitometry (QuickScan, Helena Laboratories) of orcinol-stained thin-layer chromatograms compared with authentic standards. The purity of all lipids were confirmed by thin-layer chromatography in neutral and acidic solvent systems.

Lipids were extracted from normal human lung, trachea, and WiDr cells (Krivan, H. C., Roberts, D. D., and Ginsburg, V., *Proc. Natl. Acad. Sci.*, 85, 6157–6161 (1988); Svennerholm, L. and Fredman, P., *Biochim. Biophys. Acta*. 617, 97–109 (1980)) and separated into neutral and acidic fractions by anion exchange chromatography on DEAE-Sepharose in the biocarbonate form. For some experiments, WiDr cells were metabolically labeled with [$^{35}$S]-sulfate (ICN Radiochemicals). Labeling was done for 48 h in Hams F12 medium with 10% fetal calf serum, 10% RPMI 1640, and 100 μCi/ml [$^{35}$S]-sulfate (total sulfate concentration 80 μM). Equilibration of [$^{35}$S]-sulfate with the intracellular pool in WiDr cells is complete within 4 hours (Iozzo, R. V., *J. Cell Biol.*, 99, 403–417 (1984)). The carrier sulfate concentration was selected to minimize dilution of the intracellular sulfate pool by metabolism of sulfur-containing amino acids and under sulfation due to low carrier sulfate concentrations (Iozzo, R. V., *J. Biol. Chem.*, 262, 1888–1900 (1987); Humphries, D. E., Silbert, C. K., and Silbert, J. E., *Biochem. J.*, 252, 305–308 (1988)). Thus, the specific activity of the incorporated sulfate under these conditions should equal that in the medium. Cells were removed from the tissue culture flasks by removing the medium and adding 2.5 mM EDTA in 10 mM phosphate buffered saline, pH 7.3. After 60 min. at 37° C., the cells were collected by centrifugation and extracted as described above. Desalted lipid extracts were analyzed by high performance thin layer chromatography developed in chloroform:methanol:0.25%KCl in water (5:4:1) or chloroform:methanol:acetone:acetic acid:water (8:2:4:2:1). The labeled sulfated glycolipids were visualized by autoradiography and quantified by scraping the bands and scintillation counting. Sulfated glycolipids in the tissue extracts were detected by staining of the lipids separated by high performance thin layer chromatography with $^{125}$I-von Willebrand factor (Roberts, D. D., Williams, S. B., Gralnick, H. R., and Ginsburg, V., *J. Biol. Chem.*, 261, 3306–3309 (1986)).

*Growth and Labeling of Organisms*

Virulent *M. pneumoniae* strain M129, passage 4-6, were grown and metabolically labeled with [$^3$H]palmitic acid (12-17 Ci/mmole, New England Nuclear Corp., Boston) as previously described (Chandler, D. K. F., Collier, A. M. and Barile, M. F., *Infect. Immun.*, 37–942 (1982)). The organisms were passed four times through a 26 gauge needle and suspended to approximately 10$^7$ cpm/ml of degassed RPMI 1640 medium containing 1% bovine serum albumin (Sigma, fatty acid free) and 25 mM Hepes, pH 7.3 (RPMI-BSA).

*Mycoplasma Overlay Assay*

*M. pneumoniae* were bound to glycolipids separated on thin-layer chromatograms as described in detail for other bacteria (Krivan, H. C., Roberts, D. D., and Ginsburg, V., *Proc. Natl. Acad. Sci.*, 85, 6157–6161 (1988); Krivan, H. C., Ginsburg, V. and Roberts, D. D., *Arch. Biochem. Biophys.*, 260, 493–496 (1988)). Briefly, glycolipids were separated by thin-layer chromatography on aluminum-backed silica gel high-performance plates (Merck, West Germany) developed with chloroform:methanol:0.25% CaCl$_2$ in water (60:35:8). After chromatography, the plates were coated with 0.1% polyisobutylmethacrylate, soaked in 0.05M Tris-HCl, pH 7.6, containing 110 mM sodium chloride, 5 mM CaCl$_2$, 0.2 mM phenylmethane-sulfonyl fluoride, and 1% bovine serum albumin (TBS-BSA) and incubated for 3 h at 25° C. with 60 μl /cm$^2$ of [$^3$H]-labeled *M. pneumoniae* (approximately 10$^7$ cpm/ml of RPMI-BSA). The plates were gently washed five times in 0.01M sodium phosphate, pH 7.2, containing 0.15M sodium chloride (PBS) to remove unbound organisms, dried, and exposed for 24 h to Ultrofilm $^3$H (2208-190) high speed film (LKB).

Glycolipids were chromatographed on aluminum-backed silica gel HPTLC plates developed in chloroform/methanol/0.25% CaCl$_2$ in water, 60:35:8. The plates were coated with plastic, soaked in Tris-BSA, and incubated for 3 h at 25° C. with [$^3$H]-palmitate-labeled *M. pneumoniae* suspended in RPMI 1640 containing 1% BSA and 25 mM HEPES, pH 7.3, as described in Materials and Methods (Panel A), or sprayed with orcinol reagent to identify glycolipids (Panel B). The results are shown in FIG. 1. Lane a, acidic glycolipid standards sulfatide (0.5 μg), GM3 (2 μg), GM2 (2

μg) GD1a (2 μg), GD1b (2 μg), GT1b (2 μg); lane b, neutral standards galactosyl ceramide (4 μg), lactosylceramide (4 μg), globotriaosylceramide (2 μg), and globotetraosylceramide (2 μg); lanes c and c1, sulfatide (2 μg), c$_2$ (0.5 μg) and C$_3$ (0.1 μg); lane d, seminolipid (2 μg); lane e, cholesterol 3-sulfate (2 μg); lane f, human trachea acidic glycolipids from 100 mg wet weight of tissue; lane g, monosialoganglioside from 100 mg wet weight of bovine erythrocytes; lane h, α2-3sialylparagloboside (2 μg); lane i, I-active monosialylganglioside from bovine erythrocytes (2 μg). For abbreviations see footnote 1 and Table I. The results for glycolipids tested for ability to bind M. pneumoniae are shown in Table I.

TABLE I

| Name | Binding* |
|---|---|
| Sulfatide (3SO$_4$) | +++ |
| Sulfatide (6SO$_4$) | +++ |
| Lactosylsulfatide | +++ |
| Seminolipid | +++ |
| Glucosylcer (CMH) | + |
| Lactosylcer (CDH) | ++ |
| Lacto-N-triaosylcer | + |
| Paragloboside | + |
| α-Galactosylparagloboside | + |
| Galactosylcer (CMH) | − |
| SO$_4$-Glucuronosylparagloboside | − |
| Trihexosylcer (CTH) | − |
| Asialo GM2 | − |
| Globoside (GL4) | − |
| Asialo GM1 | − |
| GM3 | − |
| GM3 (NeuGc) | − |
| GM2 | − |
| GM1 | − |
| Sialylparagloboside | − |
| Sialylparagloboside (NeuGc) | − |
| Sialylneolactofucopentaosylcer | − |
| GD1a | − |
| GD1b | − |
| GT1b | − |
| Sialylneolactohexaosylcer | − |
| I-Active Sialyllactoisooctaosylcer | − |
| I-active Lactoisooctaosylcer | − |
| I-active Gal$_2$-lactoisooctaosylcer | − |

*Negative binding (−) indicates no binding to 4 μg of lipid and positive binding to less than 0.5 μg (+++), 0.5 to 2 μg (++), and 2–4 μg (+).

Solid-Phase Binding Assay

The binding of M. pneumoniae to purified glycolipids immobilized in microtiter plates (Falcon 3912, Becton Dickinson) was measured as previously described (Krivan, H. C., Ginsburg, V. and Roberts, D. D., Arch. Biochem. Biophys., 260. 493–496 (1988)). Purified glycolipids were serially diluted in 25 μl of methanol containing 0.1 μg each of the auxiliary lipids cholesterol and phosphatidylcholine. After the solutions were dried by evaporation, the wells were filled with TBS-BSA, emptied after 1 h, rinsed with RPMI-BSA, and incubated with 25 μl of [$^3$H]-M. pneumoniae (approximately 10$^7$ cpm/ml RPMI-BSA). After incubation for 2 h at 37° C. (unless otherwise stated), the wells were washed five times with saline and bound M. pneumoniae was quantified by scintillation counting in Aquasol. For inhibition studies, various polysaccharides were serially diluted in 25 μl of RPMI-BSA in microtiter wells followed by the addition of 25 μl of [$^3$H]-M. pneumoniae.

Mycoplasma adhesion to cultured cells

Adhesion of [$^3$H]-M. pneumoniae to cells on glass covered slips was measured by a modification of a method previously described (Chandler, D. K. F., Collier, A. M., and Barile, M. F., Infect. Immun., 37–942 (1982)). WiDr human colon adenocarcinoma (ATCC CCL 218) was grown in Eagle's minimal essential medium with 10% fetal calf serum (Biofluids) in a 5% CO$_2$ atmosphere at 37° C. The cells were removed with trypsin and plated on 12 mm round glass coverslips in 24-well tissue culture plates and grown for 3 days. Control coverslips were preincubated in medium without cells. The coverslips were washed in serum-free medium then incubated in RPMI-BSA for 15 min. The medium was removed and labeled M. pneumoniae suspended in 0.5 ml of RPMI-BSA were added to each well. The plates were incubated on a rocking table for 60 min, at 37° C. The coverslips were washed by dipping in saline six times and the bound radioactive bacteria determined by scintillation counting. For inhibition studies, the inhibitors were added to M. pneumoniae prior to adding the bacteria to the coverslips.

RESULTS

Binding of M. pneumoniae to Glycolioids on Thin Layer Chromatograms

Incubation of [$^3$H]-labeled M. pneumoniae with various glycolipids resolved on thin layer chromatograms was used to determine the carbohydrate binding specificity of the organism. As shown by an autoradiogram (FIG. 1A) compared with a similar thin layer plate visualized with orcinol reagent (FIG. 1B), M. pneumoniae bound avidly to authentic sulfatide, detecting 100 ng of this glycolipid (lane c$_3$), and to a glycolipid with the same mobility as sulfatide in the acidic lipid fraction of human trachea (land f). This tracheal glycolipid was confirmed to be sulfatide by its specific staining with $^{125}$I-labeled von Willebrand factor (Roberts, D. D., Williams, S. B., Gralnick, H. R. and Ginsburg, V., J. Biol. Chem., 261, 3306–3309 (1986)). Sulfatide was also detected in human lung lipids but at lower levels than in trachea. M. pneumoniae also bound to other sulfated glycolipids including lactosyl sulfatide and seminolipid, which contain the same terminal Gal(3SO$_4$)β1-residue as sulfatide, and an isomer of sulfatide in which the terminal sulfate is linked to the 6-position of galactose. Interestingly, M. pneumoniae also binds to high amounts of lactosylceramide and to a lesser extent glucosylceramide, paragloboside, lactotriaosylceramide and α-galactosylparagloboside, but not to other neutral glycolipids (Table I). No binding was detected to other acidic glycolipids including α2-3-sialylparagloboside, I-active monosialylganglioside, or to the gangliosides GM3, GM2, GM1, GD1a, GD1b, and GT1b. In addition, sulfate itself is not sufficient for binding as M. pneumoniae does not bind to high amounts of cholesterol sulfate or to sulfated glucuronosylparagloboside, which has a terminal sulfate linked to the 3-position of glucuronic acid.

Quantitative Binding of M. pneumoniae to Immobilized Glycolipids in Microtiter Plates Binding of M. pneumoniae to purified glycolipids adsorbed on microtiter plates was examined to further define binding specificity. Binding to sulfatide was sensitive and dose-dependent (See FIG. 2). M. pneumoniae bound weakly to lactosylceramide and paragloboside, whereas no binding was detected to cholesterol sulfite or other glycolipids tested at 10 μg per well, consistent with the data obtained from the overlay assay. Binding of M. pneumoniae to sulfatide is both energy and temperature dependent (See FIG. 3). At 37° C. about 0.25 μg of sulfatide was required for half-maximum binding. The binding activity was about 5 times lower at 25° C. and was minimal at 4° C. *M. pneumoniae* also bound poorly at 37° C. in nutrient-deficient medium (Tris-BSA without RPMI) with binding activities comparable to that obtained at 4° C. (FIG. 3). These results suggest that *M. pneumoniae* requires energy and physiological temperatures for maximal binding to occur.

EXAMPLE 2

Materials

Laminin purified from the mouse Engelbreth Holm Swarm tumor was provided by Dr. Lance Liotta, NCI, NIH. Thrombospondin was purified from thrombin-stimulated human platelets (Roberts, D. D., Haverstick, D. M., Dixit, V. M., Frazier, W. A., Santoro, S. A. and Ginsburg, V., *J. Biol. Chem.*, 260, 9405-9411 (1985)). Human plasma fibronectin was from Collaborative Research, Inc. Human chorionic gonadotropin (hCG)[1] and the purified alpha subunit were provided by Drs. Bruce Weintraub and Peter Gyves, NIDDK, NIH. Most other proteins, dextran sulfate Mr 500,000, and neuraminidase (*Chlostridium perfrinoens*, Type VI) were obtained from Sigma.

6'-Sialyllactose from human milk was provided by Dr. David Smith, Department of Biochemistry and Nutrition, Virginia Polytechnic Institute and State University. 3'Sialyllactose was isolated from human milk or from a mixture of sialyllactose isomers from bovine colostrum (Boehringer Mannheim Biochemicals).

Contamination of the 6'-sialyllactose with 3'-sialyllactose was less than 2% as determined by anion exchange chromatography on an AS-6 column (Dionex Corp., Sunnyvale, Calif.).

Oligosaccharides from 500 mg of bovine fetuin (Sigma) were released by digestion in 0.2M sodium phosphate, pH 8.6, containing 10 mM B-mercaptoethanol, 1 mM EDTA, and 0.1 mM phenylmethanesulfonyl fluoride with 20 units of peptide-N (N-acetylglucosaminyl) asparagine amidase F from *Flavobacterium menincoseoticum* (Boehringer Mannheim) (Tarentino, A. L., Gomez, C. M., and Plummer, R. H., Jr., *Biochem.*, 24, 4665-4671 (1985)). For quantitative removal of asparagine-linked oligosaccharides, 10 mg of fetuin was digested with 10 units of enzyme for 48 h at 37° C. Complete release of N-linked sugars was confirmed by change in migration of the protein on SDS gel electrophoresis (Tarentino, A. L., Gomez, C. M., and Plummer, R. H., Jr., *Biochem.*, 24, 4665-4671 (1985)). Following enzyme treatment, protein was precipitated with ethanol and the oligosaccharides released from 500 mg of fetuin were desalted on Sephadex G-25 in 50 mM pyridinium acetate, pH 5, yielding 30 mg of oligosaccharides. The oligosaccharides (13 mg) were fractionated on a 25 ml column of concanavalin A Sepharose. Triantennary oligosaccharides were eluted in the void volume, and the biantennary fraction (0.5 mg) was eluted with 20 mM methyl-α-D-glucoside. The oligosaccharides were desalted by gel filtration and lyophilized. Sialic acid was determined by the periodic acid-resorcinol assay (Jourdian, G. W., Dean, L. and Roseman, J., *J. Biol. Chem.*, 246, 430-435 (1971)) and carbohydrate compositions were determined by anion exchange chromatography on a Dionex AS-6 column (Hardy, M. R., Townsend, R. R., and Lee, Y. C., *Analyt. Biochem.*, 170, 54-62 (1988)). The triantennary and biantennary fractions contained 3.2 and 1.9 moles of sialic acid per mole oligosaccharide, respectively. Analysis of the sialyloligosaccharides by anion exchange chromatography in 50 mm NaOH with 100 mM sodium acetate on a Dionex AS-6A column confirmed that the biantennary oligosaccharides were quantitatively bound on the con A column and that the biantennary fraction was free of triantennary oligosaccharides. The biantennary fraction eluted as a triplet of peaks on the AS-6A column with similar retention times as authentic biantennary disialyloligosaccharides released from human transferring and the α-subunit of hCG using peptide-N(N-acetylglucosaminyl) asparagine amidase F (Tarentino, A. L., Gomez, C. M., and Plummer, R. H., Jr., *Biochem.*, 24, 4665-4671 (1985)).

O-linked oligosaccharides from fetuin were released by alkaline borohydride degradation of 20 mg of fetuin pronase-resistant glycopeptides for 16 h at 45° C. in 1M NaBH$_4$, 0.05M NaOH (Edge, A. S. B., and Spiro, R. G., *J. Biol. Chem.*, 262, 16135-16141 (1987)). The reduced sialyloligosaccharides were purified by gel filtration on Biogel P-4 (−4,00 mesh) eluted with 50 mM pyridinium acetate, pH 5. Hexose and sialic acid were determined using the phenol-sulfuric acid (Dubois, M., Gilles, K. A., Hamilton, J. K., Rebers, P. A. and Smith, F., *Analyt. Chem.*, 28, 350-356 (1956)) and resorcinol (Jourdian, G. W., Dean, L. and Roseman, J., *J. Biol. Chem.*, 246, 430-435 (1971)) assays, respectively.

*M. pneumoniae* adhesion to immobilized glycoproteins

Glycoproteins dissolved in 0.01M sodium phosphate buffer, pH 7.4, containing 150 mM NaCl, 1 mM CaCl$_2$, and 0.01% NaN$_3$ were adsorbed onto plastic (Falcon 3912 polyvinylchloride 96 well microtiter plates) by incubation for 16 h at 4° C. Immulon 2 Removeawell plates, or Falcon 1007 bacteriological polystyrene were also used in some experiments. The unbound proteins were removed and the wells were filled with tris-BSA and incubated for 30 min at room temperature. The wells were rinsed with RPMI 1640 containing 25 mM HEPES, pH 7.3, and 1% bovine serum albumin (Sigma fatty acid free). *M. pneumoniae* strain M129 labeled with [$^3$H] palmitate (Chandler, D. K. F., Collier, A. M. and Barile, M. F., *Infect Immun.*, 35, 937-942 (1982)) were dispersed in RPMI-BSA by passing 4 times through a 26 gauge needle and 50 μl of the suspension was applied to the wells. After incubation for 60 min at 37° C., the wells were washed 5 times with saline and the labeled *M. pneumoniae* bound to the proteins were quantified by scintillation counting in Aquasol.

For inhibition studies, sugars in 25 μl of RPMI-BSA were added to wells coated with laminin (10 μg/ml) followed by 25 μl of [$^3$H]-*M. pneumoniae*. Binding was determined to both laminin-coated and uncoated wells in triplicate at each inhibitor concentration and in the absence of inhibitor. In some experiments the adsorbed proteins were pretreated with neuraminidase. After adsorption of the proteins and incubation in tris-BSA, the wells were rinsed 3 times with 50 mM sodium acetate, pH 5.5, containing 150 mM NaCl, 5 mM CaCl$_2$, 1 mg/ml bovine serum albumin, and 1 mM phenylmethanesulfonyl fluoride. The wells were incubated with 0.05 units/ml neuraminidase in the same buffer or with buffer without enzyme overnight at 20° C. The wells were rinsed three times with tris BSA, and *M. pneumoniae* binding was determined as described above.

Binding of monoclonal antibody My-28 (provided by Dr. Curt Civin, Johns Hopkins Oncology Center, Baltimore, Md.) to the immobilized proteins before or after digestion with neuraminidase was determined using a 1:1000 dilution of ascites fluid in tris-BSA. After incubation for 2 h at room temperature, the wells were washed 3 times with tris-BSA. Bound antibody was detected using goat anti-mouse IgM (Kirkegaard and Perry) labeled with $^{125}$I by the Iodogen method (Fraker, P. J. and Speck, J. C., Biochem. Biophys. Res. Commun., 80, 849-857 (1978)).

M. pneumoniae Adhesion to WiDr Cells

Adhesion of labeled M. pneumoniae to WiDr cells on glass cover slips was determined as described in the accompanying paper (Krivan, H. C., Olson,, L. D., Barile, M. F., Ginsburg, V. and Roberts, D. D., J. Biol. Chem., 264(16), 9289-9293 (1989). For inhibition studies, dextran sulfate and 3'-sialyllactose were dissolved in RPMI-BSA and the pH was adjusted to 7.4 with NaOH. The inhibitors were added to wells containing washed cover slips with attached WiDr cells or blank coverslips preincubated in medium or tris-BSA. Labeled M. pneumoniae were added immediately and incubated with slow rocking for 60 min at 37°. After washing the coverslips by dipping 6 times in saline, bound M. pneumoniae were determined by scintillation counting in Aquasol.

RESULTS

Figure 6:
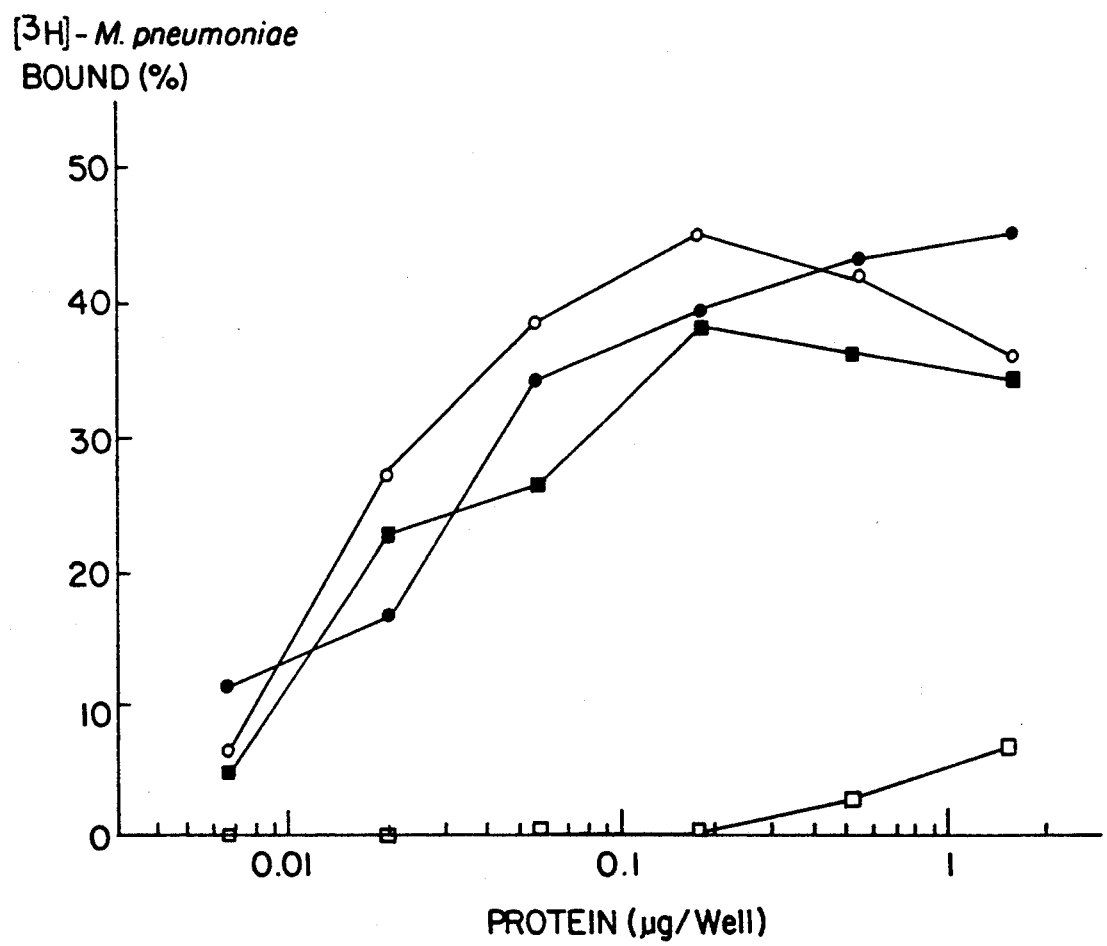
FIG. 6. M. pneumoniae binding to immobilized glycoproteins. [$^3$H]-labeled M. pneumoniae, 630,000 cpm/5×$10^5$ CCU, were incubated for 60 min at 37° C. in microtiter wells coated in duplicate with laminin (solid circle), fetuin (open circle), hCG (solid square), or transferrin (open square) at the indicated concentrations. After washing to remove the unbound organisms the bound M. pneumoniae were determined by scintillation counting. Binding to uncoated wells was 3% of the applied radioactivity.

Several glycoproteins including laminin, fetuin, and hCG support dose dependent and saturable adhesion of M. pneumoniae when adsorbed on plastic (See FIG. 6). Typically, 20 to 60% of the added M. pneumoniae bound to the wells at saturating protein concentrations. Nonspecific binding to uncoated wells was 0.3 to 3% of the total radioactivity applied. As was reported for M. pneumoniae attachment to glass substrates (Feldner, J., Bredt. W., and Razin, S., Infect. Immun., 31, 107-113 (1981)) and binding to sulfated glycolipids (Krivan, H. C., Olson, L. D., Barile, M. F., Ginsburg, V. and Roberts, D. D.), binding is energy dependent and no binding was detected in a tris-albumin buffer without glucose. Most proteins, however, are inactive in this assay (FIG. 6 and Table I). The relative activities of several proteins for promoting M. pneumoniae adhesion were estimated by comparing the dose response curves and are summarized in Table II.

TABLE II

M. pneumoniae binding to glycoproteins adsorbed on plastic

| Protein | Relative binding activity[a] |
|---|---|
| Murine Laminin | 1.5 |
| Bovine Fetuin | 1.0 |
| PNGase F-treated Fetuin | 0.09 |
| hCG | 0.7 |
| hCG α-subunit | 0.8 |
| Human platelet thrombospondin | 0.7 |
| Human type MM glycophorin | 0.06 |
| Human $\alpha_1$-acid glycoprotein | 0.03 |
| Hen Ovomucoid | <0.01 |
| Human Transferrin | <0.01 |
| Human plasma Fibrinogen | <0.01 |
| Human plasma Fibronectin | <0.01 |
| Bovine serum Albumin | <0.01 |

[a]Binding of [$^3$H]-M. pneumoniae was determined to polyvinyl chloride microtiter wells coated with 0.006 to 2 μg of the respective proteins. Relative binding activities of the proteins were determined by the amount of protein required to give half maximal binding of labeled M. pneumoniae (typically 10-30% of the total added) and are expressed relative to fetuin which was included as a positive control in each experiment and was assigned a value of 1.0. Results are the mean values of 2 or 3 experiments for each protein.

The proteins laminin, fetuin, thrombospondin, hCG, and the α-subunit of hCG have similar activity and promote adhesion to wells coated with less than 10 ng of glycoprotein. Glycophorin and $\alpha_1$-acid glycoprotein are weakly active, whereas the other proteins are essentially inactive, promoting binding of less than 10% of the added M. pneumoniae at the highest levels tested (1-5 μg/well).

Immulon 2 microtiter plates and bacteriological polystyrene were also examined as substrates for M. pneumoniae adhesion to adsorbed proteins. Although binding varied with the plastic used, the distinction between the active and inactive glycoproteins was consistently observed with all three types of plastic. Thus, the differences in activity are probably not an artifact of selective adsorption of the active glycoproteins.

N-Deglycosylated fetuin was tested in the assay to examine the role of the O-linked sialyloligosaccharides of fetuin in adhesion of M. pneumoniae (Table II). The protein promoted adhesion of M. pneumoniae at higher concentrations but was approximately 10-fold less active than intact fetuin. The low activity of glycophorin (Table II) also suggests that βc2-3-linked sialic acid on 0-linked oligosaccharides is not as active as on N-linked oligosaccharides.

Figure 7:
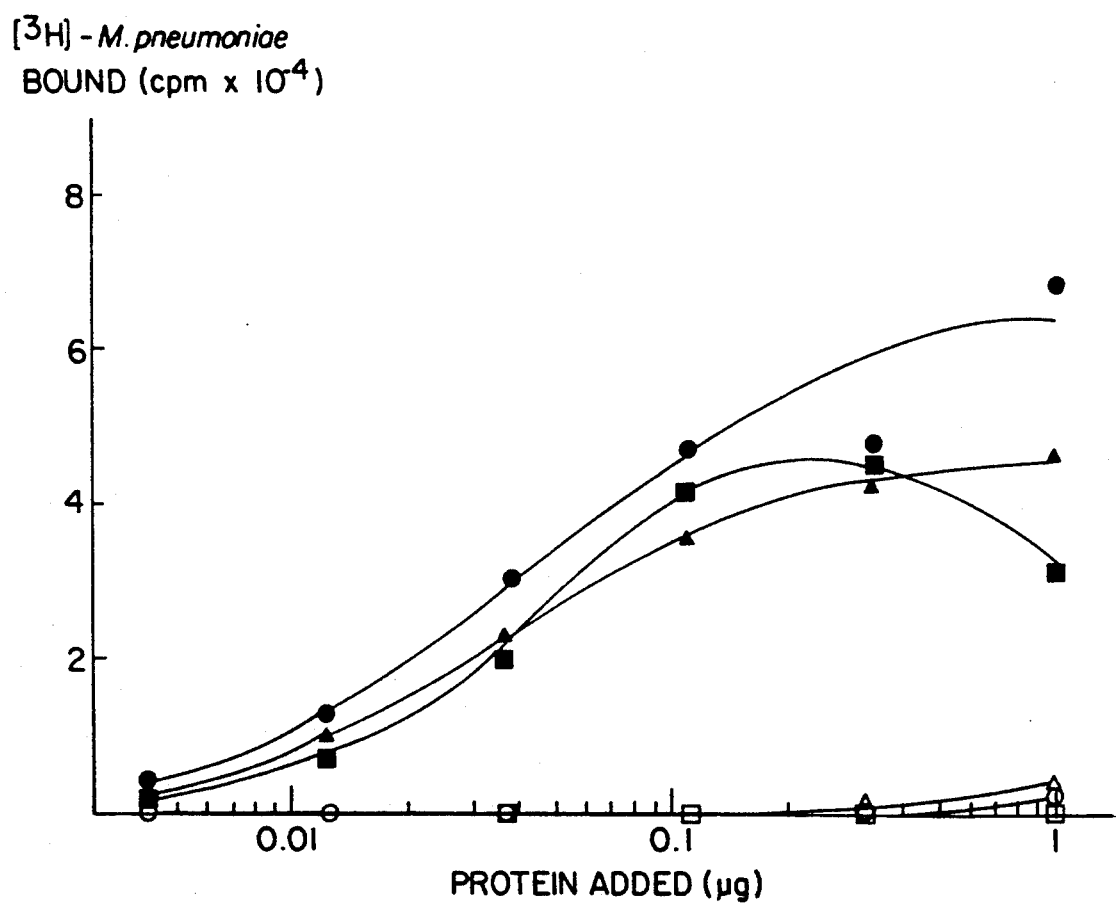
FIG. 7. Effect of neuraminidase treatment on M. pneumoniae binding to immobilized glycoproteins. Microtiter wells were coated with fetuin (circles), hCG (squares), or α-subunit of hCG (triangles) and treated for 16 h with 0.05 U/ml neuraminidase (open symbols) in sodium acetate buffer pH 5.5 or buffer alone (closed symbols). [$^3$H]-labeled M. pneumoniae binding was determined as described in Materials and Methods.
Figure 8:
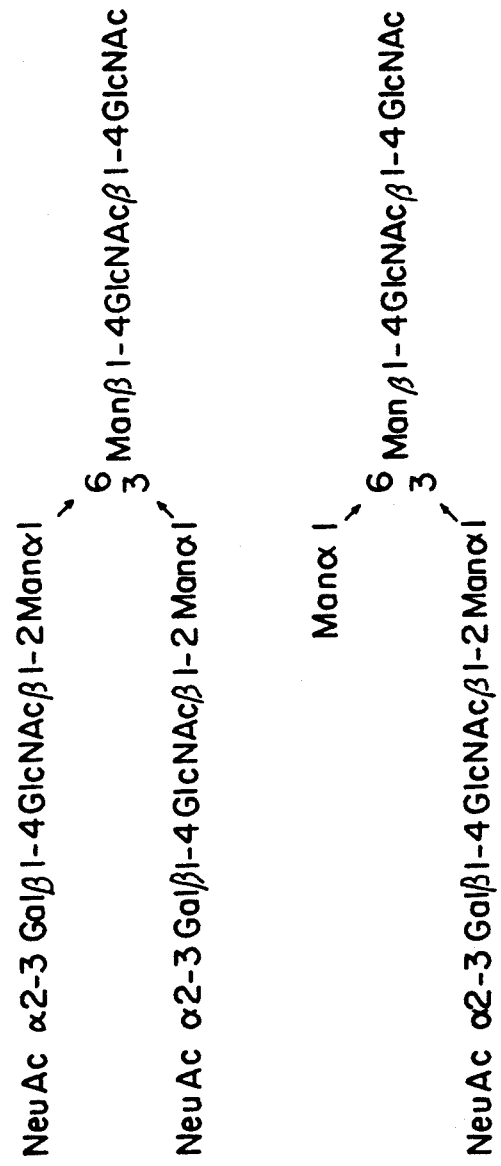
FIG. 8. Structures of sialylated oligosaccharides on the α subunit of human chorionic gonadotropin (23) proposed to mediate M. pneumoniae adhesion. The biantennary oligosaccharide is the minimal structure required for binding based on the present results. It is not known whether the monoantennary oligosaccharide can bind M. pneumoniae with high affinity.
Figure 9:
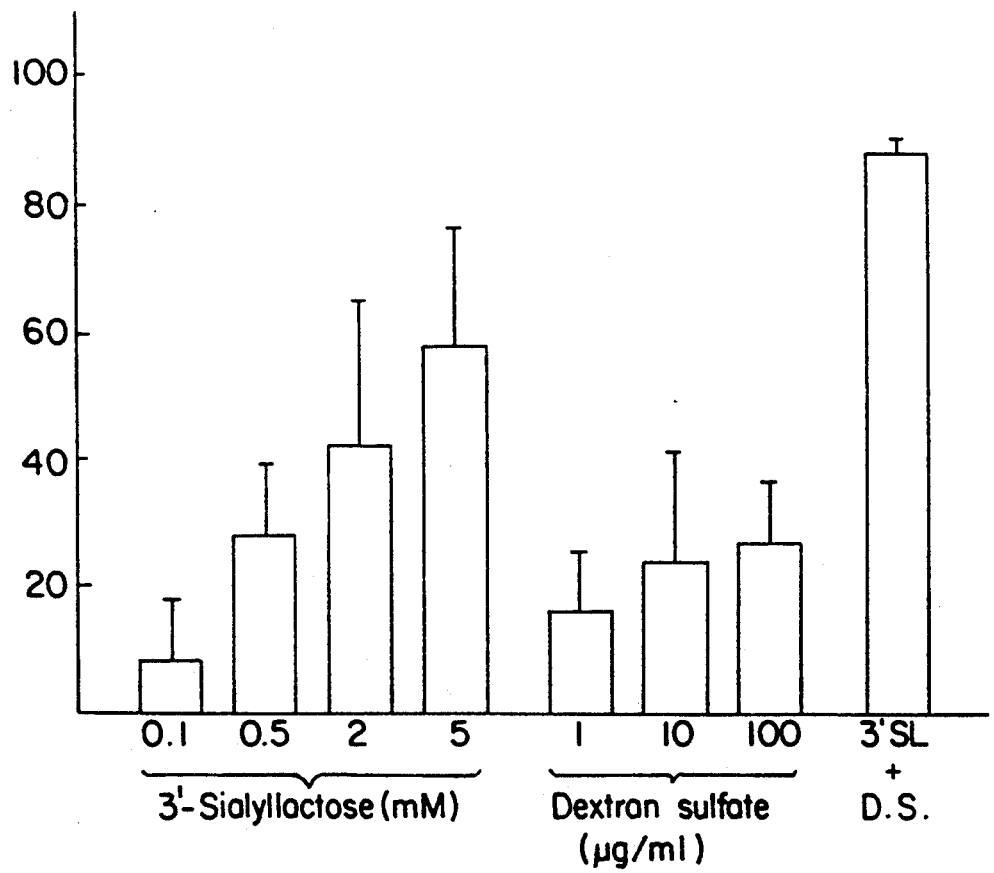
FIG. 9. Inhibition of M. pneumoniae adhesion to the human adenocarcinoma WiDr cell line. Adhesion of [$^3$H]-M. pneumoniae to WiDr cells growing on 13 mm glass cover slips was determined as described in Materials and Methods. Inhibition by dextran sulfate or 3'-sialyllactose at the indicated concentrations or by a combination of 100 μg/ml dextran sulfate and 5 mM 3'-sialyllactose (3'S L+D. S.) was calculated relative to control binding determined in RPMI/BSA without inhibitors. Results are presented as percent inhibition (mean±S. D. n=4 with n=8 for determination of control binding without inhibitors).

Binding to all of the active glycoproteins requires sialic acid, as neuraminidase treatment of the adsorbed proteins (FIG. 7) or pretreatment with neuraminidase in solution before adsorption (results not shown) abolishes all binding activity. Several of the inactive glycoproteins also contain sialic acid but the linkage reported in human transferring (Spik, G., Bayard, B., Fournet, B., Strecker, G., Bouquelet, S. and Montreuil, J., FEBS Lett., 50, 296-299 (1975)), fibrinogen (Townsend, R. R., Hilliker, E., Li, Y-T., Laine, R. A., Bell, W. R. and Lee, Y. C., J. Biol. Chem., 257, 9704-9710 (1982)), and plasma fibronectin (Takasaki, S., Yamashita, K., Suzuki, K. and Kobata, A., J. Biochem. Tokyo, 88, 1587-1594 (1980)) is exclusively α2-6 to galactose. The linkage in hCG (Endo, Y., Yamashita, K., Tachibana, Y., Tojo, S. and Kobata, A., J. Biochem. Tokyo, 669-679 (1979)) and a majority of N-linked fetuin oligosaccharides (Nilsson, B., Norden, N. E., and Svensson, S., J. Biol. Chem., 254, 4545-4553 (1979); Takasaki, S. and Kobata, A., Biochemistry, 25, 5709-5715 (1986); Townsend, R. R., Hardy, M. R., Wong, T. C. and Lee, Y. C., Biochemistry, 25, 5716-5725 (1986)) is α2-3. Thus, in agreement with previous studies of erythrocyte adhesion to surface grown sheet cultures of M. pneumoniae (4), binding of the labeled M. pneumoniae to immobilized glycoproteins appears to be specific for α2-3-linked sialic acid.

With the exception of hCG, all of the active glycoproteins have extensive heterogeneity in their carbohydrate structures or have only partially characterized structures. hCG contains only mono- and biantennary asparagine-linked oligosaccharides on both subunits (Endo, Y., Yamashita, K., Tachibana, Y., Tojo, S., and Kobata, A., J. Biochem. Tokyo, 85, 669-679 (1979); Mizuochi, T. and Kobata, A., Biochem. Biophys. Res. Commun., 97, 772-778 (1980)) and 4 O-linked oligosaccharides on the β-subunit (Kessler, M. J., Mise, T., Ghai, R. D., and Bahl, O. P., J. Biol. Chem., 254, 7909-7914 (1979)). Since the β-subunit of hCG binds M. pneumoniae as well as the intact protein (Table I and FIG. 7), the O-linked carbohydrates on the B-subunit are not required for binding. Thus, a biantennary asparagine linked carbohydrate with α2-3-linked sialic acid is sufficient for binding of M. pneumoniae.

EXAMPLE 3

In generally the same manner as described above various bacteria were tested for their ability to bind to GalNAcβ1-4Gal sequences found in fucosylasialo-GM1, asialo-GM1 and asialo-GM2. The results are shown in the following table.

| Microorganism | Binding* |
|---|---|
| Streptococcus pneumoniae 33400 | + |
| Streptococcus pneumoniae 6303 | + |
| Streptococcus pneumoniae 27336 | + |
| Staphylococcus aureus 12600 | + |
| Staphylococcus aureus 8095 | + |
| Haemophilus influenzae 33391 | + |
| Haemophilus influenzae 9795 | + |
| Haemophilus parainfluenzae 33392 | + |
| Klebsiella pneumoniae 27736 | + |
| Pseudomonas aeruginosa CT3 | + |
| Pseudomonas aeruginosa CT4 | + |
| Pseudomonas aeruginosa CT5 | + |
| Pseudomonas aeruginosa 17648 | + |
| Pseudomonas aeruginosa 19142 | + |
| Pseudomonas aeruginosa 33347 | + |
| Pseudomonas aeruginosa 21472 | + |
| Pseudomonas cepacia 25416 | + |
| Pseudomonas cepacia ML1 | + |
| Pseudomonas cepacia 13945 | + |
| Pseudomonas maltophilia 13637 | + |
| Escherichia coli VJ1 | + |
| Escherichia coli 6883 | + |
| Mycoplasma pneumoniae M129 | − |
| Streptococcus pyogenes 12344 | − |
| Salmonella milwaukee U4 4407-50 | − |
| Salmonella enteritidis 13076 | − |
| Escherichia coli K1 | − |
| Escherichia coli K99 1472 (B44) | − |

*Bacteria were tested for binding to glycosphingolipids by the bacterial overlay assay. Plus (+) indicates binding and minus (−) indicates no binding to at least 2 μg of glycosphingolipid containing the GalNAcβ1-4Gal sequence.

EXAMPLE 4

Figure 10:
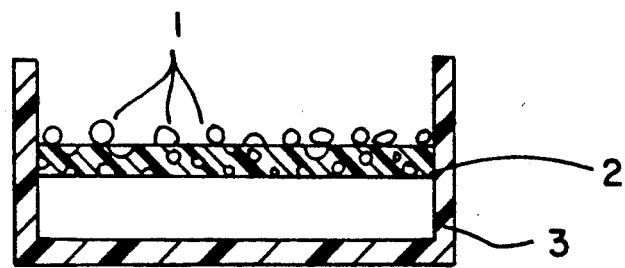
FIG. 10 is a cross-sectional view of a preferred device for practicing the invention.

The following predictive Example constitutes a preferred manner for carrying out the present invention as shown in FIG. 10. Latex particles 1 coated with carbohydrate receptors which bind to E. coil (prepared by the method described by de Man et al, *J. Clin. Micb.*, 25, 401–406 (1987), the entire contents of which are hereby incorporated by reference) are immobilized on a porous membrane 2 which is supported in a container 3. The particles are present in an amount sufficient to bind E. coli which may contact the particles but not in an amount so great as to "clog" the membrane or destroy its porosity. A liquid sample suspected of containing E. coli is poured onto the top of the membrane and passes across said latex particles and through said porous membrane whereby E. coli, if present, will adsorb to the carbohydrate receptors on the latex particles. A solution containing a labelled antibody against E. coli (e.g., an antibody conjugated to an enzyme) is then passed across said latex particles and through said membrane. A wash solution is then passed across said latex particles and through said membrane to wash any unbound labelled antibody off the membrane. If the label is an enzyme, a substrate for said enzyme is then contacted with said membrane. If the enzyme conjugated antibody is bound in said membrane to the latex particles, the enzyme substrate will turn color thereby indicating the presence of the microorganisms. If the label is a fluorescent or radioactive material, another suitable test is employed to detect the presence of the labelled antibody.

What is claimed is:

1. A method for detecting the presence of *Mycoplasma pneumoniae* in a sample which comprises:
   contacting said sample with a carbohydrate receptor immobilized on an insoluble support, said carbohydrate receptor being a glycolipid selected from the group consisting of Gal(3SO₄)β1-1Cer, Gal(6SO₄)β1-1Cer, Gal(3SO₄)β1-4Glcβ1-1Cer, Gal(3SO₄)β1-3alkylaclglycerol, GlcNAcβ1-3Galβ1-4Glcβ1-1Cer and Galβ1-4GlcNAcβ1-3Galβ1-4Glcβ1-1Cer, for a time and under conditions sufficient for Mycoplasma pneumoniae present in said sample to bind to said carbohydrate receptor thereby forming a complex on said support;
   adding a labelled reagent to said support wherein said labelled reagent binds to the complex; and
   detecting the presence of the labelled reagent bound to said support as a means of detecting the presence of Mycoplasma pneumoniae in said sample.

2. The method of claim 1, wherein said carbohydrate receptor is Gal(3SO₄)β1-1Cer.

3. The method of claim 1, wherein said carbohydrate receptor is Gal(6SO₄)β1-1Cer.

4. The method of claim 1, wherein said carbohydrate receptor is Gal(3SO₄)β1-4Glcβ1-1Cer.

5. The method of claim 1, wherein said carbohydrate receptor is Gal(3SO₄)β1-3alkylacylglycerol.

6. The method of claim 1, wherein said carbohydrate receptor is GlcNAcβ1-3Galβ1-4Glcβ1-1Cer.

7. The method of claim 1, wherein said carbohydrate receptor is Galβ1-4GlcNAcβ1-3Galβ1-4Glcβ1-1Cer.

8. A method of detecting the presence of a microorganism in a sample wherein said microorganism is selected from the group consisting of *Streptococcus pneumoniae*, *Hemophilus influenzae*, *Pseudomonas aeruginosa*, *Pseudomonas cepacia* and *Pseudomonas maltophilia*, which comprises:
   contacting said sample with a carbohydrate receptor immobilized on an insoluble support, said carbohydrate receptor being a glycolipid selected from the group consisting of GalNAcβ1-4Galβ1-4Glcβ1-1Cer, Galβ1-3GalNAcβ1-4Galβ1-4Glcβ1-1Cer and Fucα1-2Galβ1-3GalNAcβ1-4Galβ1-4Glcβ1-1Cer, for a time and under conditions sufficient for said microorganism present in said sample to bind said carbohydrate receptor thereby forming a complex on said support;
   adding a labelled reagent to said support wherein said labelled reagent binds to the complex; and
   detecting the presence of the labelled reagent bound to said support as a means of detecting the presence of said microorganism in said sample.

9. The method of claim 8, wherein said microorganism is Streptococcus pneumoniae.

10. The method of claim 8, wherein said microorganism is Hemophilus influenzae.

11. The method of claim 8, wherein said microorganism is Pseudomonas aeruginosa.

12. The method of claim 8, wherein said microorganism is Pseudomonas cepacia.

13. The method of claim 8, wherein said microorganism is Pseudomonas maltophilia.

14. The method of claim 8, wherein said carbohydrate receptor is GalNAcβ1-4Galβ1-4Glcβ1-1Cer.

15. The method of claim 8, wherein said carbohydrate receptor is Galβ1-3GalNAcβ1-4Galβ1-4Glcβ1-1Cer.

16. The method of claim 8, wherein said carbohydrate receptor is Fucα1-2Galβ1-3GalNAcβ1-4Galβ1-4Glcβ1-1Cer.

* * * * *